US008945574B2

(12) United States Patent
Mistrello et al.

(10) Patent No.: US 8,945,574 B2
(45) Date of Patent: Feb. 3, 2015

(54) **HYPOALLERGENIC VARIANTS OF THE MAJOR ALLERGEN FROM *BETULA VERRUCOSA* POLLEN**

(75) Inventors: Giovanni Mistrello, Milan (IT); Stefania Zanotta, Milan (IT); Daniela Roncarolo, Milan (IT); Paolo Falagiani, Milan (IT)

(73) Assignee: Lofarma S.p.A., Milan (IT)

( * ) Notice: Subject to any disclaimer, the term of this patent is extended or adjusted under 35 U.S.C. 154(b) by 1195 days.

(21) Appl. No.: 12/159,528

(22) PCT Filed: Dec. 19, 2006

(86) PCT No.: PCT/EP2006/012237
§ 371 (c)(1),
(2), (4) Date: Apr. 24, 2009

(87) PCT Pub. No.: WO2007/073907
PCT Pub. Date: Jul. 5, 2007

(65) Prior Publication Data
US 2009/0304752 A1    Dec. 10, 2009

(30) Foreign Application Priority Data
Dec. 29, 2005  (IT) .............................. MI2005A2517

(51) Int. Cl.
*A61K 38/00*  (2006.01)
*A61K 39/00*  (2006.01)
*A61K 39/35*  (2006.01)
*C07K 1/00*   (2006.01)
*C07K 14/00*  (2006.01)
*C07K 17/00*  (2006.01)
*C07K 14/415* (2006.01)
*A61K 39/36*  (2006.01)

(52) U.S. Cl.
CPC .............. *C07K 14/415* (2013.01); *A61K 39/36* (2013.01)
USPC ....... 424/185.1; 424/275.1; 514/1.1; 530/350

(58) Field of Classification Search
None
See application file for complete search history.

(56) References Cited

U.S. PATENT DOCUMENTS

| 6,610,297 | B1 * | 8/2003 | Kricek et al. .............. 424/178.1 |
| 2004/0043438 | A1 * | 3/2004 | Holm et al. .................. 435/7.92 |

FOREIGN PATENT DOCUMENTS

| WO | WO 94/10194     | * | 5/1994  | ............. C07K 7/08 |
| WO | WO 99/47680 A1  |   | 9/1999  |                        |
| WO | WO 02/40676 A1  | * | 5/2002  | ............. C12N 15/29 |
| WO | WO 02/40676 A2  |   | 5/2002  |                        |
| WO | WO 03/096869 A2 |   | 11/2003 |                        |

OTHER PUBLICATIONS

Blumenthal et al. 'Definition of an Allergen.' Allergens and Allergen Immunotherapy. Ed. R Lockey, S. Bukantz and J. Bousquet. New York: Marcel Decker, 2004.37-50.*
Skolnick et al. 'From genes to protein structure and function: novel applications of computational approaches in the genomic era.' Trends in Biotech. 18:34-39, 2000.*
Attwood et al. 'The Babel of Bioinformatics.' Science 290(5491):471-473, 2000.*
Kuby et al. 'Immunology.' Fourth Edition, Chapter 18: 449-465, 2000.*
Radauer et al. 'The Bet v 1 fold: an ancient, versatile scaffold for binding of large, hydrophobic ligands.' BMC Evolutionary Biology. 8:286-304, 2008.*
Maleki et al. 'The effects of roasting on the allergenic properties of peanut proteins.' J. Allerg. Clin. Immunol. 106:763-768, 2000.*
H.-J. Malling, "Immunotherapy as an effective tool in allergy treatment," Allergy 1998: 53: 461-472.
E. Toubi, et al. "Follow-up after systemic adverse reactions of immunotherapy," Allergy 1999, 54, 617-620.
Cezmi A. Akdis, et al. "Regulation of Specific Immune Responses by Chemical and Structural Modifications of Allegens," Int Arch Allergy Immunol 2000; 121:261-269.
Heimo Breiteneder, et al. "The gene coding for the major birch pollen allergen Betvl, is highly homologous to a pea disease resistance response gene," The EMBO 1989; 8(7): 1935-1938.
Rudolf Valenta, et al. "Identification of Profilin as a Novel Pollen Allergen; IgE Autoreactivity in Sensitized Individuals," Science 1991; 253:557-560.
Thierry Batard, et al. "Characterization of Wild-Type Recombinant Bet v 1a as a Candidate Vaccine against Birch Pollen Allergy," Int Arch Allergy Immunol 2005; 136:239-249.
Ines Swoboda et al., "Isoforms of Bet v 1, the Major Birch Pollen Allergen, Analyzed by Liquid Chromatography, Mass Spectrometry, and cDNA Cloning," Journal of Biological Chemistry 1995; 270(6): 2607-2613.
I. Swoboda et al., "cDNA cloning and characterization of three genes in the Bet v 1 gene family that encode pathogenesis-related proteins," Plant, Cell and Environment 1995;18:865-874.
Zora Marković-Housley et al., "Crystal Structure of a Hypoallergenic Isoform of the Major Birch Pollen Allergen Bet v 1 and its Likely Biological Function as a Plant Steroid Carrier," J. Mol. Biol. (2003) 325: 123-133.
Verena Niederberger, MD et al., "Recombinant birch pollen allergens (rBet V1 and rBet v 2) contain most of the IgE epitopes present in birch, alder, hornbeam, hazel, and oak pollen: A quantitative IgE inhibition study with sera from different populations," J Allergy Clin Immunol 1998;102:579-91.
Philipp Neudecker et al., "Mutational epitope analysis of Pru av 1 and Api g 1, the major allergens of cherry (*Prunus avium*) and celery (*Apium graveolens*): correlating IgE reactivity with three-dimensional structure," Biochem. J. 2003; 376:97-107.

(Continued)

*Primary Examiner* — Nora Rooney
(74) *Attorney, Agent, or Firm* — Arent Fox LLP (57) ABSTRACT

The invention provides hypoallergenic variants of Bet v 1 major allergen from *Betula verrucosa* plant pollen and the use thereof for the preventive or therapeutic treatment of allergic diseases.

2 Claims, 5 Drawing Sheets

(56) References Cited

OTHER PUBLICATIONS

R. Asero, "Effects of birch pollen-specific immunotherapy on apple allergy in birch pollen-hypersensitive patients," Clinical and Experimental Allergy, 1998; 28:1368-1373.

Vincenzo Visco et al., "Human IgG Monoclonal Antibodies That Modulate the Binding of Specific IgE to Birch Pollen Bet v 1[1]," The Journal of Immunology, 1996; 157: 956-962.

Susanne Vrtala et al., "Immunization with Purified Natural and Recombinant Allergens Induces Mouse IgG1 Antibodies That Recognize Similar Epitopes as Human IgE and Inhibit the Human IgE-Allergen Interaction and Allergen-Induced Basophil Degranulation," J Immunol 1998; 160:6137-6144.

"Two-Stage PCR Protocol Allowing Introduction of Multiple Mutations, Deletions and Insertions Uisng QuikChange Site-Directed Mutagenesis," Bio Techniques 1999; 26:680-682.

Younghee Kim, Cloning and Expression of a Lipase Gene from Rice (*Oryza sativa* cv. Dongjin), Molecules and Cells 2004; 18(1): 40-45.

J. A. Asturias et al., "PCR-based cloning and immunological characterization of *Parietaria judaica* pollen profilin," J Invest Allergol Clin Immunol 2004; vol. 14(1): 43-48.

Harry Towbin et al., "Electrophoretic transfer of proteins from polyacrylamide gels to nitrocellulose sheets: Procedure and some applications," Proc. Natl. Acad. Sci. USA 1979; 76(9):4350-4354.

M. Breitenbach at al., "Biological and Immunological Importance of Bet v 1 Isoforms," New Horizons in Allergy Immunotherapy, A. Sheon et al., eds., Plenum Press, New York, 1996; Chapter 16, pp. 117-126.

F. Ferreira et al., "Isoforms of Atopic Allergens with Reduced Allergenicity but Conserved T Cell Antigenicity: Possible Use for Specific Immunotherapy," Int Arch Allergy Immunol 1997; 113:125-127.

Fátima Ferreira et al., "Dissection of Immunoglobulin E and T Lymphocyte Reactivity of Isoforms of the Major Birch Pollen Allergen Bet v 1: Potential Use of Hypoallergenic Isoforms for Immunotherapy", Journal of Experimental Medicine, Tokyo, JP, vol. 183, No. 2, Feb. 1996, pp. 599-609, XP009011302, ISSN: 0022-1007.

Fátima Ferreira et al., "Modulation of IgE Reactivity of Allergens by Site-Directed Mutagenesis: Potential Use of Hypoallergenic Variants for Immunotherapy" FASEB Journal, Fed. of American Soc. for Experiemental Biology, Bethesda, MD. US, vol. 12, No. 2, Feb. 1998, pp. 231-242, XP002085249.

* cited by examiner

Figura 4

Figure 5

SEQUENCE LISTING

<160> NUMBER OF SEQ ID NOS: 14

<210> SEQ ID NO 1
<211> LENGTH: 159
<212> TYPE: PRT
<213> ORGANISM: Betula verrucosa

<400> SEQUENCE: 1

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Asn Asn Lys Tyr His Thr Lys Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

<210> SEQ ID NO 2
<211> LENGTH: 159
<212> TYPE: PRT
<213> ORGANISM: Betula verrucosa

<400> SEQUENCE: 2

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Ala Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Asn Asn Lys Tyr His Thr Lys Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

```
<210> SEQ ID NO 3
<211> LENGTH: 159
<212> TYPE: PRT
<213> ORGANISM: Betula verrucosa

<400> SEQUENCE: 3

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Ala Ile Asn Asn Lys Tyr His Thr Lys Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

<210> SEQ ID NO 4
<211> LENGTH: 159
<212> TYPE: PRT
<213> ORGANISM: Betula verrucosa

<400> SEQUENCE: 4

Gly Val Phe Asn Tyr Glu Thr Glu Thr Thr Ser Val Ile Pro Ala Ala
1               5                   10                  15

Arg Leu Phe Lys Ala

<213> ORGANISM: Betula verrucosa

<400> SEQUENCE: 5

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Ala Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Ala Ile Asn Asn Lys Tyr His Thr Ala Gly Asp His Glu Val
        115                 120                 125

Lys Ala Glu Gln Ile Lys Ala Ser Lys Glu Met Gly Glu Thr Leu Leu
130                 135                 140

Arg Ala Val Glu Ser Tyr Leu Leu Ala His Ser Asp Ala Tyr Asn
145                 150                 155

<210> SEQ ID NO 6
<211> LENGTH: 480
<212> TYPE: DNA
<213> ORGANISM: Betula verrucosa

<400> SEQUENCE: 6

```
ggtgttttca attacgaaac tgagaccacc tctgttatcc cagcagctcg actgttcaag      60
gcctttatcc ttgatggcga taatctcttt ccaaaggttg caccccaagc cattagcagt     120
gttgaaaaca ttgaaggaaa tggagggcct ggaaccatta gaagatcag  ctttcccgaa     180
ggcttcccctt tcaagtacgt gaaggacaga gttgatgagg tggaccacac aaacttcaaa    240
tacaattaca gcgtgatcga gggcggtccc ataggcgaca cattggagaa gatctccaac    300
gagataaaga tagtggcaac ccctgatgga ggttccatct tgaagatcaa caacaagtac    360
cataccaaag gagaccatga ggtgaaggca gagcagatta aggcaagtaa agaaatggga    420
gagacacttt tgagggccgt tgagagctac ctcttggcac actccgatgc ctacaactaa    480
```

<210> SEQ ID NO 7
<211> LENGTH: 480
<212> TYPE: DNA
<213> ORGANISM: Betula verrucosa

<400> SEQUENCE: 7

```
ggtgttttca attacgaaac tgagaccacc tctgttatcc cagcagctcg actgttcaag      60
gcctttatcc ttgatggcga taatctcttt ccaaaggttg caccccaagc cattagcagt     120
gttgaaaaca ttgaaggaaa tggagggcct ggaaccattg cgaagatcag  ctttcccgaa    180
ggcttcccctt tcaagtacgt gaaggacaga gttgatgagg tggaccacac aaacttcaaa   240
tacaattaca gcgtgatcga gggcggtccc ataggcgaca cattggagaa gatctccaac    300
gagataaaga tagtggcaac ccctgatgga ggttccatct tgaagatcaa caacaagtac    360
cataccaaag gagaccatga ggtgaaggca gagcagatta aggcaagtaa agaaatggga    420
```

-continued

<210> SEQ ID NO 8
<211> LENGTH: 480
<212> TYPE: DNA
<213> ORGANISM: Betula verrucosa

<400> SEQUENCE: 8

```
ggtgttttca attacgaaac tgagaccacc tctgttatcc cagcagctcg actgttcaag      60
gcctttatcc ttgatggcga taatctcttt ccaaaggttg caccccaagc cattagcagt     120
gttgaaaaca ttgaaggaaa tggagggcct ggaaccatta agaagatcag ctttcccgaa     180 ggcttcccctt tcaagtacgt gaaggacaga gttgatgagg tggaccacac aaacttcaaa    240
tacaattaca gcgtgatcga gggcggtccc ataggcgaca cattggagaa gatctccaac    300
gagataaaga tagtggcaac ccctgatgga ggttccatct tggcgatcaa caacaagtac    360
cataccaaag agaccatga ggtgaaggca gagcagatta aggcaagtaa agaaatggga     420
gagacacttt tgagggccgt tgagagctac ctcttggcac actccgatgc ctacaactaa    480
```

<210> SEQ ID NO 9
<211> LENGTH: 480
<212> TYPE: DNA
<213> ORGANISM: Betula verrucosa

<400> SEQUENCE: 9

```
ggtgttttca attacgaaac tgagaccacc tctgttatcc cagcagctcg actgttcaag      60
gcctttatcc ttgatggcga taatctcttt

-continued

```
<213> ORGANISM: Artificial Sequence
<220> FEATURE:
<223> OTHER INFORMATION: Description of Artificial Sequence: Synthetic
      primer

<400> SEQUENCE: 11
cctggaacca ttgcgaagat cagctttccc                                          30

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggttccatct tggcgatcaa caacaagtac c                                        31

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagtaccata ccgcaggaga ccatgag                                             27

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5
```

HYPOALLERGENIC VARIANTS OF THE MAJOR ALLERGEN FROM *BETULA VERRUCOSA* POLLEN

CROSS-REFERENCE TO RELATED APPLICATION

This is a National Stage entry of International Application No. PCT/EP2006/012237, filed Dec. 19, 2006, which claims priority to Italian Application No. MI2005A002517, filed Dec. 29, 2005. The disclosures of the prior applications are hereby incorporated herein in their entirety by reference.

The present invention provides hypoallergenic sequence variants of the Bet v 1 protein, nucleic acid molecules encoding them, pharmaceutical compositions containing the same and their use in the prophylaxis and therapy of allergic diseases caused by pollen of plants from *Betula verrucosa* species.

BACKGROUND OF THE INVENTION

Allergies are caused by a dysfunction in the immune system, which reacts to innocuous proteins contained in pollen, mites, epithelia and certain foods by producing IgE-class antibodies.

Recent data indicate that above 10% of the population in Western countries suffers from this disease, the symptoms of which may deteriorate with time giving rise to e.g. asthma or a sensitization to other allergens thus making more difficult the choice of the appropriate therapy.

Specific hyposensitizing immunotherapy, unlike pharmacological therapy, is the only etiological treatment of allergic diseases capable of favourably changing the immunological parameters on which these diseases are based.

The hyposensitizing immunotherapy consists in the administration of increasing doses of standardized extracts (vaccines) obtained from the same substance which causes the disease (1). In this way, a sort of immunological tolerance to said substance is gradually induced in the patient with following disappearance of the allergic symptoms.

However, the risk of eliciting serious side effects (2), although remarkably reduced with the use of either slow-release vaccines or vaccines administered through routes alternative to injections, has in fact limited the application of specific hyposensitizing immunotherapy in the treatment of allergic diseases.

In recent years, most attention has been focused on the development of effective, safer vaccines. In particular, the development of vaccines consisting of mutagenized recombinant proteins, i.e. hypoallergenic variants capable of favourably influencing the natural progression of the disease without causing undesired side effects (3), has represented an important goal.

The pollen of plants taxonomically known as Fagales (birch, alder, hazel, oak, hornbeam) is one of the most important causes of allergic rhinitis and asthma in the temperate regions. The two major allergens of birch pollen, Bet v 1 (cDNA deposited at GenBank acc. No. X15877) and Bet v 2 (acc. No. M65179) are proteins with molecular weight of 17 and 14 kD, respectively (4,5). Nearly 95% of patients with allergy to birch pollen produce IgE antibodies against Bet v 1 and 60% of these patients show reactivity against Bet v 1 alone (6).

Bet v 1 is naturally present in over ten isoforms showing a sequence identity comprised between 84.4% and 99.4% (7). This allergen belongs to the family of 'pathogenesis related proteins', i.e. ubiquitous proteins produced by plants in response to environmental or pathology stress, the functions of which is supposed to be connected to steroid transport (8,9). The high sequence homology with the allergens of group 1 in pollen from other plants of the Fagales order explains why patients with IgE specific for Bet v 1 show allergic symptoms during the pollination season of different plants belonging to the same taxonomic order (10). The allergy to birch pollen is often accompanied by adverse reactions provoked by intake of fresh fruits (e.g. cherry, apple, pear) or vegetables (e.g. celery and carrot). The reason is that such foods contain proteins characterized by high sequence and structure homology to Bet v 1, which are recognized by specific IgEs raised by the birch major allergen (11). The immunotherapy with Bet v 1 allergen may be effective in the treatment of birch pollen allergy as well as pollinosis to other plants of the order Fagales and allergy to food containing allergens that cross-react with Bet v 1 (12).

A factor correlating to the beneficial effects of the hyposensitizing immunotherapy is the induction of IgG antibodies specific for the sensitizing allergen. Such (protecting) antibodies can inhibit the IgE binding to the antigen, specifically to Bet v 1, altering the tridimensional conformation of this molecule (13, 14). The development of vaccines consisting of recombinant proteins possessing less allergenicity and unaltered immunogenic properties would ameliorate the therapy of allergic diseases.

DESCRIPTION OF THE INVENTION

It has now been found that by replacing or deleting one or more amino acid residues within the protein sequence of the Bet v 1 allergen, this becomes less reactive to the IgE antibodies.

In a first aspect, the invention provides a hypoallergenic protein which is a sequence variant of the Bet v 1 allergen, characterized by:
1) showing reduced reactivity to IgEs compared to wild-type Bet v 1 allergen (SEQ ID NO:1);
2) having an amino acid sequence which:
   a) is at least 87%, preferably at least 94%, more preferably at least 97% identical to SEQ ID NO: 1;
   b) in a sequence alignment with SEQ ID NO:1, presents at least one substitution or deletion of the residues corresponding to amino acids 54, 115 and/or 123 of SEQ ID NO:1, wherein a Lys residue is present.

The variants of the Bet v 1 allergen that, according to the invention, display 1, 2 or 3 Lys-substitutions and/or deletions at the indicated positions and are referred to as single-, double- or triple substitution and/or deletion variants, respectively. Substitution rather than deletion variants are preferred, especially those in which at least one Lys residue at the indicated positions is replaced with a neutral or polar amino acid. More preferably, said neutral or polar amino acid is selected from Ala, Thr, Gly, Pro, Leu, Ile, Ser, Phe, yet more preferably from Ala, Thr and Ser.

In a preferred embodiment, the hypoallergenic protein consists of SEQ ID NO:1 bearing said at least one substitution or deletion of Lys residues at positions 54, 115 and 123.

Typical hypoallergenic proteins bearing 1 or 3 substitutions according to the invention are identified in SEQ ID NO:2, SEQ ID NO:3, SEQ ID NO:4 and SEQ ID NO:5.

Bet v 1 allergen substitution and/or deletion variants according to the invention, compared to the wild-type counterpart, show a IgE reactivity reduction by at least 25%, preferably at least 50%, more preferably at least 80%, to the serum of *Betula verrucosa* pollen-allergic patients.

Figure 1:
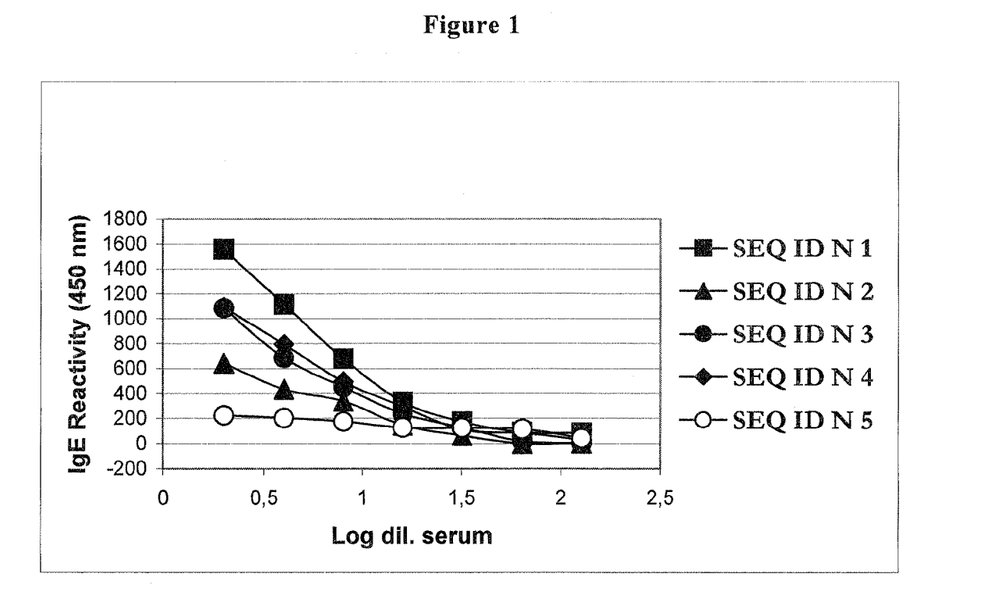
FIG. 1: ELISA analysis of IgE reactivity to Bet v 1 allergen and to Bet v 1 hypoallergenic variants.

The IgE reactivity of the proteins SEQ ID NOs:2-5 from a pool of sera of allergic patients was tested in an ELISA assay (FIG. 1). Compared to the wt Bet v 1 allergen (SEQ ID NO:1), a 56% (SEQ ID NO:2), 34% (SEQ ID NO:3), 28% (SEQ ID NO:4) and 80% (SEQ ID NO:5) mean reduction of IgE reactivity was observed when such proteins were incubated with various dilutions (from 1:2 to 1:8) of serum pools from patients allergic to birch pollen.

Figure 2:
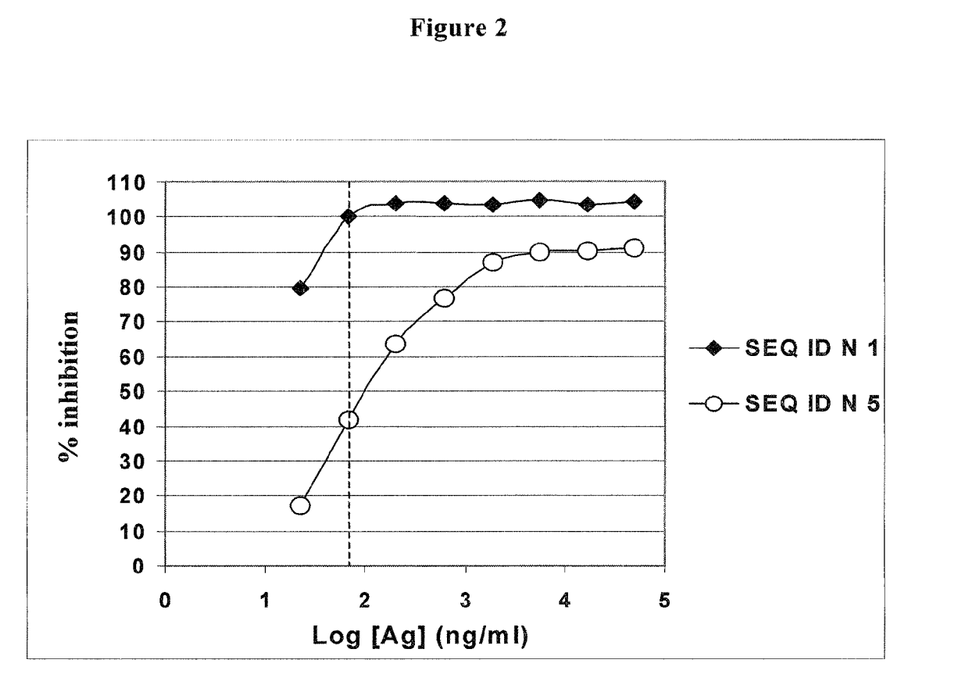
FIG. 2: Inhibition of IgE binding to Bet v 1 allergen.

These results were confirmed by experiments of ELISA inhibition, which allow to evaluate the reactivity of homologous epitopes from different proteins. The binding of Bet v 1 wt (SEQ ID NO:1) to IgEs from a serum pool is inhibited by 100% when the serum is pre-treated with the same protein while the observed inhibition is only 40% when the serum is pre-incubated with identical amounts of triple-substitution variant (SEQ ID NO:5) (FIG. 2). These results clearly indicate that the amino acid substitutions at positions 54, 115 and 123 of SEQ ID NO:1 diminish the recognition of Bet v 1 allergen by IgEs.

Figure 3:
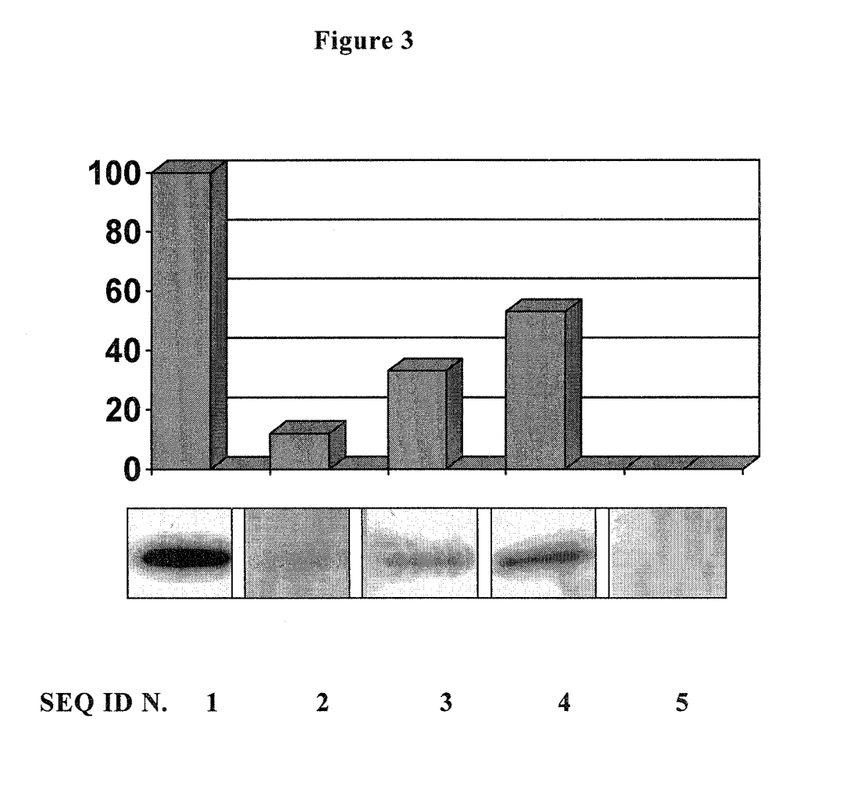
FIG. 3: Western blotting analysis of IgE reactivity to Bet v 1 allergen and variants thereof.

Furthermore, the reactivity of SEQ ID NOs:2-5 proteins to IgEs from a serum pool positive to *Betula verrucosa* pollen was assayed by Western Blotting. Also in this case, a reduction of IgE reactivity was observed in the analyzed sera, which, compared to wt Bet v 1 (SEQ ID NO:1), was 88% for SEQ ID NO:2, 67% for SEQ ID NO:3, 47% for SEQ ID NO:4 and 100% for SEQ ID NO:5 (FIG. 3).

Figure 4:
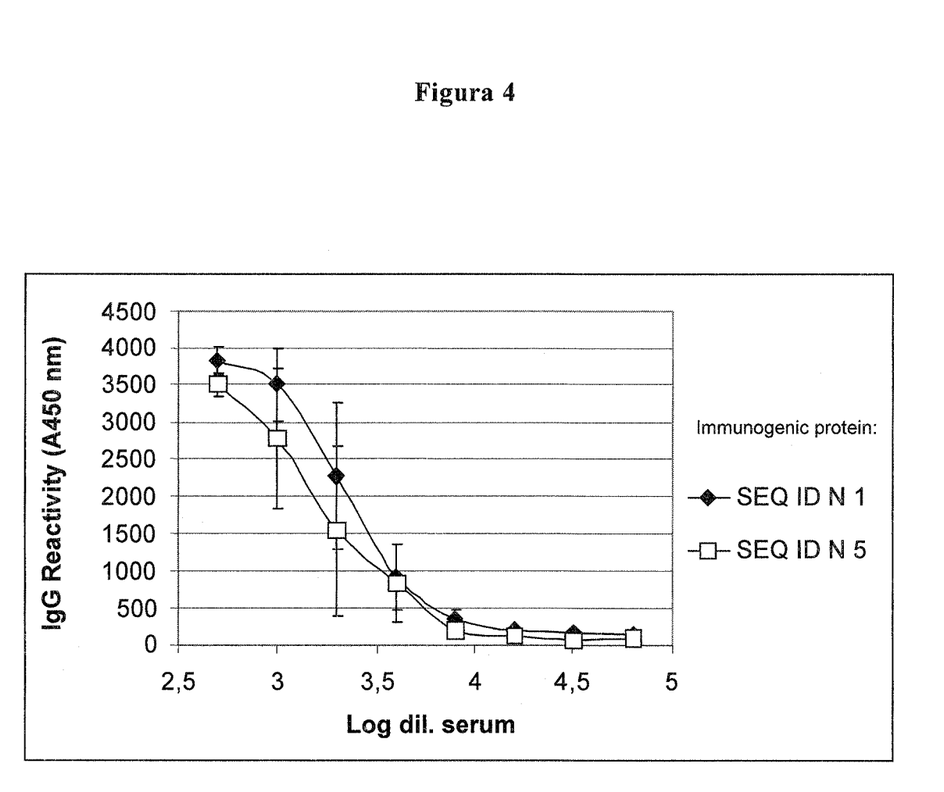
FIG. 4: Murine IgG response to respective immunogenic proteins.

In addition, in experiments of Balb/c mouse immunization, both the Bet v 1 wt allergen and the hypoallergenic protein SEQ ID NO:5 proved able to induce a IgG-specific immune response (FIG. 4). In particular, the antibodies against SEQ ID NO:5 were able to recognize the wt-counterpart SEQ ID NO:1 (FIG. 5), suggesting that the replacement of Lys-residues at positions 54, 115 and/or 123 does not determine a significant alteration of the protein immunogenicity and particularly of its IgG epitopes. In contrast, the antibodies present in the serum of mice immunized with a non-correlated antigen were not able to recognize either wt Bet v 1 or SEQ ID NO:5.

In a further aspect, the invention provides an immunologically active peptide corresponding to a Bet v 1 fragment containing from 15 to 35, more preferably from 15 to 20 amino acid residues and carrying at least one of the above-described substitutions and/or deletions. As used herein, the expression "immunologically active peptide" indicates a peptide that is able to elicit a IgE-independent immune response.

Substitution and/or deletion variants according to the invention can be easily prepared by mutagenesis of Bet v 1 cDNA sequence (SEQ ID NO:6) using methods and techniques known to any one skilled in the art.

The cDNA sequences coding for the single and triple substitution variants SEQ ID NOs:2-5 are identified in SEQ ID NOs:7-10, respectively.

In further aspects the invention provides a nucleic acid molecule encoding a hypoallergenic Bet v 1 protein herein disclosed, or a peptide derived therefrom, and an expression vector containing said nucleic acid molecule functionally linked to genetic elements controlling the expression of said protein or peptide in eukaryotic or prokaryotic cells, such as transcription promoters, enhancers, signal and leader sequences or other sequences involved in transcription regulation. Examples of vectors include plasmids, viruses and phages but any other vector that is commonly utilized in genetic engineering may be employed as well.

The invention further comprises a prokaryotic or eukaryotic host cell which is transformed or transfected with a vector as above described. Prokaryotic cells such as *Escherichia coli* or *Bacillus subtilis*, or eukaryotic cells such as *Saccharomyces cerevisiae* are generally used for vector cloning and cDNA expression.

In addition, the hypoallergenic variants according to the invention can be produced as fusion proteins.

Thanks to their reduced IgE-reactivity, the Bet v 1 variants according to the present invention can be conveniently used for the preparation of pharmaceutical compositions (e.g. tablets and capsules) for the preventive or therapeutic treatment of individuals allergic to *Betula verrucosa* pollen.

In a further aspect the invention is therefore directed to a pharmaceutical composition containing an effective amount of hypoallergenic Bet v 1 variant as herein provided, optionally in combination with other allergens of *Betula verrucosa* and/or with pharmaceutically acceptable vehicles and excipients. In a preferred embodiment of the invention, the pharmaceutical composition is in the form of a vaccine to be used in the prophylaxis or therapy of allergic diseases, including bronchial asthma, allergic rhinitis, allergic dermatitis and allergic conjunctivitis. The theory and practice of vaccination are known to anyone skilled in the art (15, 16).

The following examples further illustrate the invention. Unless otherwise indicated, the methods used in the examples are described in Sambrook, Fritsch E T Maniatis "Molecular cloning. A laboratory manual" II ed. Vol. 1-2-3 CSH Lab Press 1989.

EXAMPLE 1

Site-Specific Mutagenesis of the cDNA Coding for Bet v 1 Allergen

Site-specific mutagenesis of the cDNA coding for the Bet v 1 allergen (SEQ ID NO: 6) was carried out by cDNA cloning in a prokaryotic vector (pBluescript, GenBank acc. n. X52327) followed by PCR amplification. The oligonucleotides used as primers in the PCR reaction (Table) carried the appropriate base substitutions. For each mutagenesis, a complementary oligonucleotide binding to a corresponding region of the DNA strand was used (17). After amplification, the unaltered original template was selectively degraded with enzymatic digestion catalyzed by the restriction enzyme DpnI. *Escherichia coli* cells were then transformed with the mutagenized molecules. Clones obtained from single bacterial colonies were sequenced according to Sanger to determine the correct base modification and the absence of non-specific mutations in the cDNA.

TABLE

Sequences of the oligonucleotides (SEQ ID NOS 11-13, respectively, in order of appearance) used as primers in site-specific mutagenesis.

| Oligonucleotide | Sequence |
|---|---|
| Bet v 1 54 | cct gga acc att gcg aag atc agc ttt ccc |
| Bet v 1 115 | ggt tcc atc ttg gcg atc aac aac aag tac c |
| Bet v 1 123 | aag tac cat acc gca gga gac cat gag |

The mutated bases are in bold character.

EXAMPLE 2

Production of Bet v 1 Protein and Variants Thereof

Wild-type (SEQ ID N. 6) and mutagenized (SEQ ID N. 7-10) Bet v 1 cDNAs, flanked by a sequence coding for six histidines (SEQ ID NO: 14), were cloned and expressed in *Escherichia coli* according to standard protocols (18, 19). The cells were collected by centrifugation, resuspended in a 50 mM $NaH_2PO_4$, 300 mM NaCl buffer, pH 8, and lysed by sonication. The recombinant proteins were separated by centrifugation. The pellet containing an insoluble protein aggregate was resuspended in 100 mM $NaH_2PO_4$, 10 mM Tris-HCl, 8 M urea (pH 8) (denaturing buffer) and stirred for 60 min. The solubilized recombinant proteins were separated from insoluble debris by centrifugation and purified by affinity chromatography under denaturing conditions using agarose columns linked to nitrilotriacetic acid, which chelates the nickel ions interacting with the six-histidine (SEQ ID NO: 14) portion fused to the allergen. The purified proteins were refolded by dialysis for 16 hours at 4° C. in 0.68% NaCl, 0.275% $NaHCO_3$ solution.

EXAMPLE 3

Characteristics of Sera from Allergic Subjects

Sera were collected from individuals with clinical anamnesis of seasonal allergy to *Betula verrucosa* pollen and a RAST 4+ specific reactivity to *B. verrucosa* allergens and then they were pooled. A pool of sera from non-allergic patients was used as negative control.

EXAMPLE 4

ELISA Analysis of Bet v 1 Variants Reactivity to IgEs from a Serum Pool

The same quantity of wt allergen and of mutagenized variants (0.5 μg) in 50 mM carbonate/bicarbonate buffer, pH 9.6, were adsorbed on wells of polystirene plates for ELISA assay by incubation at 4° C. for 16 hours. The wells were washed with washing solution (60 mM phosphate buffer, pH 6.5, containing 0.05% Tween-20), and blocked with diluting solution (25% horse serum, 1 mM EDTA, 0.05% Tween 20, 0.01% Thiomersal in 150 mM phosphate buffer, pH 7.4). 100 μl aliquots of serial dilutions (in dilution buffer) of a pool of human sera RAST 4+ were added to each sample and incubated at 25° C. for 2 hours. After three washes, peroxidase-conjugated anti human-IgE serum (1:1500 in diluting buffer) was added, followed by incubation at 25° C. for 1.5 hours. After three washes, the colorimetric reaction was developed by adding 100 μl of TMB reagent (BioFX Laboratories, Owings Mills, Md.) and incubating for 15 minutes at 25° C. The reaction was stopped by adding 100 μl of 1 N HCl and read at 450 nm using a microplate reader spectrophotometer.

EXAMPLE 5

ELISA-Inhibition Assay. Bet v 1 Variants Inhibition of Wt Bet v 1 Binding to IgEs from Serum Pools 1 μg aliquots of wt allergen in 50 mM carbonate/bicarbonate buffer, pH 9.6, were adsorbed on wells of polystyrene plates for ELISA assay by incubation at 4° C. for 16 hours. The wells were washed with washing solution (60 mM phosphate buffer, pH 6.5, containing 0.05% Tween-20) and blocked with diluting buffer (25% horse serum, 1 mM EDTA, 0.05% Tween 20, 0.01% Thiomersal in 150 mM phosphate buffer, pH 7.4). 100 μl aliquots of RAST 4+ human serum pool diluted 1:3 in dilution buffer were pre-incubated at 25° C. for 2 hours with serial dilutions of wt allergen and of mutagenized variant. The obtained solution was placed in the wells and incubated at 4° C. for 16 hours. After three washes with 0.06 M phosphate buffer pH 6.5, Tween-20 0.05%, the peroxidase-conjugated anti-human IgE serum was added at 1:1500 dilution (in diluting buffer), followed by incubation at 25° C. for 1.5 hours. After three washes, the colorimetric reaction was developed by adding 100 μl TMB reagent (BioFX Laboratories, Owings Mills, Md.) and incubating at 25° C. for 15 minutes. The reaction was stopped by adding 100 μl HCl 1 N followed by spectrophotometric reading at 450 nm.

The inhibition percentage was calculated as follows: $100 \times [(A-B)/A]$, wherein A is the absorbance at 450 nm in the absence of inhibitor while B is the absorbance in the presence of inhibitor.

EXAMPLE 6

Western Blot Analysis of Bet v 1 Variants Reactivity to IgEs from a Serum Pool Equal amounts of wild-type allergen and mutagenized forms (1.5 μg) were electrophoretically analyzed on polyacrylamide gel followed by electroblotting on nitrocellulose membrane, as described by Towbin (20).

The membrane was first incubated for one hour in TBST (TBS, 0.05% Tween-20) containing 5% non-fat dry milk (saturation buffer) and then incubated overnight with a pool of sera from subjects allergic to *Betula verrucosa* showing a 4+ reactivity, diluted 1:3 in TBST 2% non-fat dry milk. After 1-hr incubation, the membrane was washed three times with TBST. The membrane-bound antibodies were contacted with peroxidase-conjugated anti-human IgE serum and, after several washes, detected with the chemiluminescence detection system using luminol as the peroxidase substrate (ECL, Amersham).

EXAMPLE 7

Protocol for Immunization of Balb/c Mice

Two groups of 5 female Balb/c mice (Charles River) were subcutaneously immunized with 200 μl of an emulsion containing 100 μl complete Freund adjuvant and 20 μg antigen (SEQ ID NO:1 and SEQ ID NO:5) in 100 μl saline. Three additional booster immunizations were carried out at 1-week intervals replacing the complete adjuvant with an incomplete one. As a control, five mice were administered a non-correlated antigen. Seven days after the last immunization, a blood sample was taken from the tail and used in ELISA to control the antibody response against each immunogenic agent. In mice immunized with SEQ ID NO:5, the capability to recognize the wild-type protein was also analyzed.

EXAMPLE 8

Elisa Analysis of IgG-Specific Response in Immunized Mice

The same quantities of wt Bet v 1 and of SEQ ID NO:5 variant (0.25 μg) in 50 mM carbonate/bicarbonate buffer, pH 9.6, were adsorbed on wells of polystyrene plates for ELISA assay by incubation for 16 hours at 4° C. The wells were washed with washing solution (60 mM phosphate buffer, pH 6.5, containing 0.05% Tween-20) and blocked with diluting solution (25% horse serum, 1 mM EDTA, 0.05% Tween 20, 0.01% Thiomersal in 150 mM phosphate buffer, pH 7.4). 100 µl aliquots of serial dilutions (in dilution buffer) of serum from each mouse were placed in the wells and incubated for 2 hours at 25° C.

Figure 5:
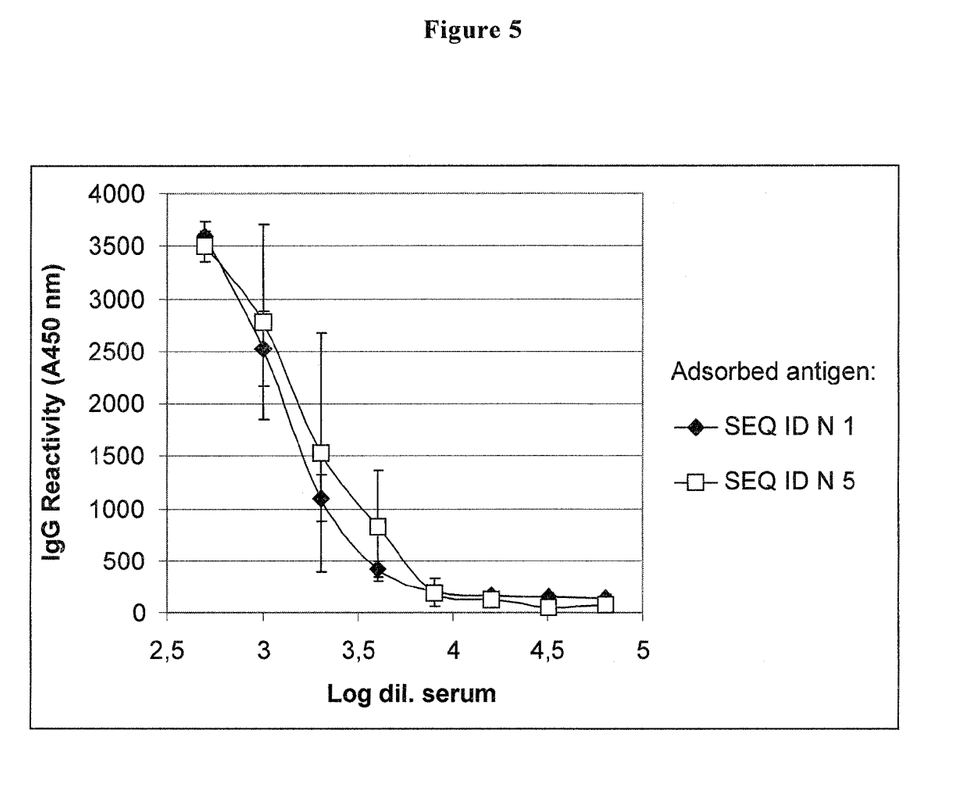
FIG. 5: IgG response in mice immunized with SEQ ID NO:5.

After three washes, the peroxidase-conjugated anti mouse IgG serum was diluted 1:2000 in dilution buffer and added to the wells, followed by incubation for 1.5 hr at 25° C. After three washes, the colorimetric reaction was developed by adding 100 µl of TMB reagent (BioFX Laboratories, Owings Mills, Md.) and incubating for 15 min at 25° C. The reaction was stopped with 100 µl HCl 1 N followed by spectrophotometric reading at 450 nm. FIGS. 4 and 5 show the mean reactivity obtained by analysis of the sera from 5 mice for each group.

BIBLIOGRAPHY

1) Malling H. J., (1998) "Immunotherapy as an effective tool in allergy treatment". Allergy, 53: 461.
2) Toubi E., Kessel A., Blant A., Golan T. D., (1999) "Follow-up after systemic adverse reactions of immunotherapy". Allergy, 54(6): 617-620.
3) Akdis C. A., Blaser K., (2000) "Regulation of specific immune response by chemical and structural modifications of allergens". Int. Arch. Allergy Immunol., 121(4): 261-269.
4) Breiteneder H., Pettenburger K., Bito A et al. (1989). "The gene coding for the major birch pollen allergen Bet v 1, is highly homologous to a pea disease resistance response gene". EMBO J, 8: 1935-1938.
5) Valenta R., Duchene M., Pettenburger K., Sillaber C., Valent P., Bettelheim P., Breitenbach M., Rumpold H., Kraft D., Scheiner O. (1991). "Identification of profilin as a novel pollen allergen; IgE autoreactivity in sensitized individuals." Science 253:557-560.
6) Batard T., Didierlaurent A., Chabre H., et al., (2005). "Characterization of wild-type recombinant Bet v 1a as a candidate vaccine against birch pollen allergy". Int Arch Allergy Immunol. 136: 239-249.
7) Swoboda I., Jilek A., Ferreira F., Engel E., Hoffmann-Sommergruber K., Scheiner O., Kraft D., Breiteneder H., Pittenauer E., Schmid E., Vicente O., Heberle-Bors E., Ahorn H., Breitenbach M. (1995). "Isoforms of Bet v 1, the major birch pollen allergen, analyzed by liquid chromatography, mass spectrometry, and cDNA cloning". JBC. 270 (6): 2607-2613.
8) Swoboda I., Scheiner O., Heberle-Bors E., Vicente O., (1992). "cDNA cloning and characterisation of three genes in the Bet v 1 gene family that encode pathogenesis-related proteins". Plant Cell Environ. 18: 865-874.
9) Markovic-Housley Z., Degano M., Lamba D., von Roepenack-Lahaye E., Clemens S., Susani M., Ferreira F., Scheiner O., Breiteneder H. (2003). "Crystal structure of a hypoallergenic isoform of the major birch pollen allergen Bet v 1 and its likely biological function as a plant steroid carrier. J Mol Biol, 325: 123-133.
10) Niederberger V., Pauli G., Gronlund H. et al. (1998). "Recombinant birch pollen allergens (rBet v 1 and rBetv 2) contain most of the IgE epitopes present in birch, alder, hornbeam, hazel, and oak pollen: a quantitative IgE inhibition study with sera from different populations". J Allergy Clin Immunol. 102: 579-591.
11) Neudecker P, Lehmann K, Nerkamp J, Haase T, Wangorsch A, Fotisch K, Hoffmann S, Rosch P, Vieths S, Scheurer S. (2003). "Mutational epitope analysis of Pru av 1 and Api g 1, the major allergens of cherry (*Prunus avium*) and celery (*Apium graveolens*): correlating IgE reactivity with three-dimensional structure". Biochem J. 376(Pt 1):97-107.
12) Asero R. (1998). "Effects of birch pollen-specific immunotherapy on apple allergy in birch pollen hypersensitive patients". Clin Exp Allergy. 28: 1368-1373.
13) Visco V, Dolecek C, Denépoux S, Le Mao J, Guret C, Rousset F, Guinnepain M T, Kraft D, Valenta R, Weyer A, Banchereau J, Lebecque S. (1996). "Human IgG monoclonal antibodies that modulate the binding of specific IgE to birch pollen Bet v 1". J. Immunol. 157: 956-962.
14) Vrtala S, Ball T, Spitzauer s, Pandjaitan B, Suphioglu C, Knox B, Sperr W R, Valent P, Kraft D, Valenta R. (1998). "Immunization with purified natural and recombinant allergens induces mouse IgG1 antibodies that recognize similar epitopes as human IgE and inhibit the human IgE-allergen interaction and allergen-induced basophil degranulation". J Immunol 160: 6137.
15) Paul, (1989), "Fundamental Immunology", Raven press, New York.
16) Cryz, S. J. (1991), "Immunotherapy and Vaccines", VCH Verlagsgesellschaft.
17) Wang W., Malcolm B A. (2002). "Two-stage polymerase chain reaction protocol allowing introduction of multiple mutations, deletions, and insertions, using QuikChange site-directed mutagenesis". Methods Mol. Biol.; 182: 37-43.
18) Younghee Kim. (2004). "Cloning and Expression of a Lipase Gene from Rice (*Oryza sativa* cv. Dongjin)". Mol. Cells, 18 (1): 40-45.
19) Asturias J A, Ibarrola I, Eseverri J L, Arilla M C, Gonzales-Rioja R, Martinez A. (2004). "PCR-based cloning and immunological characterization of *Parietaria judaica* pollen profilin". J Investig Allergol Clin Immunol, 14: 43-48.
20) Towbin J., Staehelin T., Gordon J., (1979). "Electrophoretic transfer of proteins from polyacrylamide gels to nitrocellulose sheets: Procedure and some applications". Proc. Natl. Acad. Sci. USA, 76: 4350-4354.

The invention claimed is:

1. A protein which is a hypoallergenic variant of the major allergen of *Betula verrucosa* pollen (Bet v 1), wherein the protein is selected from the group consisting of SEQ ID NOs: 2-5.

2. A pharmaceutical composition comprising an effective amount of a protein according to claim 1, and excipients.

* * * * *